(12) United States Patent
Pressman

(10) Patent No.: US 6,423,863 B1
(45) Date of Patent: Jul. 23, 2002

(54) METHOD OF SUSTAINING CATALYST ACTIVITY IN THE CATALYTIC PRODUCTION OF AROMATIC CARBONATES

(75) Inventor: Eric James Pressman, East Greenbush, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/681,940

(22) Filed: Jun. 28, 2001

(51) Int. Cl.[7] .............................................. C07C 69/96
(52) U.S. Cl. ...................................... 558/274; 558/270
(58) Field of Search ................................. 502/185, 316, 502/317, 325; 558/270, 274

(56) References Cited

U.S. PATENT DOCUMENTS 5,498,789 A 3/1996 Takagi et al. ............... 558/270

*Primary Examiner*—Robert W. Ramsuer
*Assistant Examiner*—Ebenezer Sackey
(74) *Attorney, Agent, or Firm*—Norren C. Johnson; Christian G. Cabou

(57) ABSTRACT

The present invention is directed to a method for sustaining the catalytic activity of a carbonylation catalyst composition, after changes in reactor pressure and temperature, in the catalytic production of aromatic carbonates.

26 Claims, No Drawings

METHOD OF SUSTAINING CATALYST ACTIVITY IN THE CATALYTIC PRODUCTION OF AROMATIC CARBONATES

BACKGROUND OF INVENTION

The present invention is directed to a method for sustaining the catalytic activity of a catalyst composition, and in particular to a method for sustaining the catalytic activity of a catalyst composition used in the production of aromatic carbonates.

A useful method for the production of aromatic carbonates includes the oxidative carbonylation of aromatic hydroxy compounds, with carbon monoxide and oxygen, which is typically catalyzed by a catalyst composition comprising a Group 8, 9 or 10 metal catalyst, various metal co-catalysts, a salt source, optionally an activating solvent, and optionally a base source. The oxidative carbonylation of aromatic hydroxy compounds is typically performed under elevated reactor pressures between about 5 MPa and about 15 MPa, due to the low solubility of both carbon monoxide and oxygen in typical aromatic hydroxy reagents such as phenol, and elevated reactor temperatures between about 50° C. and about 120° C. to accelerate reaction rates. On a commercial scale, the oxidative carbonylation of aromatic hydroxy compounds could be facilitated if reaction conditions, such as temperature and pressure, could be periodically varied during the course of the reaction, e.g., during temporary reactor shutdown periods, without reducing the activity of the catalyst composition. However, what is typically observed when the elevated pressure in a catalytic oxidative carbonylation reaction of an aromatic hydroxy compound is temporarily reduced to about atmospheric pressure, specifically at reaction mixture temperatures above about 60° C. is an irreversible decrease in the activity of the catalyst composition once the original reaction conditions are re-established. Consequently, a long felt yet unsatisfied need exists for new and improved methods for sustaining the activity of catalyst compositions during and after changes in the reaction conditions of a catalytic oxidative carbonylation reaction.

SUMMARY OF INVENTION

In one embodiment, the present invention is directed to a method for sustaining the catalytic activity of a carbonylation catalyst composition, after changes in reaction conditions, in a catalytic oxidative carbonylation reaction contained in a reactor vessel in which a reaction mixture comprising said carbonylation catalyst composition is disposed, said method comprising the following steps: interrupting said carbonylation reaction with a first reaction condition changing step, which comprises first lowering the temperature of the reaction. mixture from a first temperature T1, to a second temperature T2, followed by lowering the pressure in said reactor vessel from a first pressure P1, to a second pressure P2; optionally, a resting step, which comprises maintaining said reaction mixture at said second temperature T2, and maintaining the pressure in said reactor vessel at said second pressure P2, for a predetermined amount of time; andre-establishing said carbonylation reaction with a second reaction condition changing step, which comprises first raising the pressure in said reactor vessel from said second pressure P2 to a third pressure P3, followed by raising the temperature of said reaction mixture from said second temperature T2 to a third temperature T3; wherein the level of catalytic activity of said carbonylation catalyst composition under said third temperature T3, and said third pressure P3, is comparable to a level of catalytic activity which would be present in an equivalent catalytic oxidative carbonylation reaction in which the temperature and pressure were changed from said first temperature T1 and said first pressure P1 directly to said third temperature T3 and said third pressure P3, in the absence of said first reaction condition changing step, and said optional resting step.

DETAILED DESCRIPTION

The method of the present invention is suitable for a typical carbonylation catalyst compositions comprising a Group 8, 9, or 10 catalyst source, which can catalyze the production of aromatic carbonates via the oxidative carbonylation of aromatic hydroxy compounds with oxygen and carbon monoxide.

In one embodiment, the present invention is directed to a method for sustaining the catalytic activity of a carbonylation catalyst composition, after changes in reaction conditions in a catalytic oxidative carbonylation reaction. In the context of the present invention, the phrase "sustaining the catalytic activity" is defined as prolonging the amount of time during which the catalyst composition is active at producing the desired aromatic carbonate at a predetermined reaction rate. The "predetermined reaction rate" is a rate which is comparable, e.g., having a value that is between about 80% and about 120% of the reference value, to a reaction rate that would be present in a similar oxidative carbonylation reaction in the absence of any changes to the reaction conditions. Herein, the reaction rate is defined in terms of the weight percent of desired aromatic carbonate produced during a predetermined amount of reaction time, e.g., weight % of desired carbonate=[(moles of desired carbonate)(molecular weight of desired carbonate)/mass of reaction mixture].

In the context of the present invention, the term "reaction conditions" is meant to include, but is not limited to, reactor vessel pressure, reactor vessel temperature, reaction mixture temperature, agitation rate, gas flow rates (e.g., carbon monoxide flow rate and oxygen flow rate), gas mixture composition (e.g., ratio of carbon monoxide to oxygen), the weight % of various components of the reaction mixture including, but not limited to, weight % of aromatic hydroxy compound, weight % of desired carbonate and weight % of water, and the pH of the reaction mixture.

In the present invention, the term "reaction mixture" is defined as the total mixture of compounds and gases which results from the carbonylation of an aromatic hydroxy compound using oxygen, carbon monoxide, and a carbonylation catalyst composition typically comprising a Group 8, 9 or 10 metal source as a catalyst, and optionally at least one member selected from the group consisting of a first inorganic co-catalyst (IOCC), a second IOCC, a salt source, an activating solvent, a base source, and any mixtures thereof. During the carbonylation reaction, the reaction mixture typically further comprises the desired aromatic carbonate, unreacted aromatic hydroxy compound, and byproducts of the carbonylation reaction which include, but are not limited to, water, aryl ethers, poly-aromatic hydroxy compounds, phenyl salicylate, and aromatic carbonates other than the desired aromatic carbonate. Suitable types of aromatic hydroxy compounds include, but are not limited to, monocyclic aromatic compounds comprising at least one hydroxy group, and polycyclic aromatic compounds comprising at least one hydroxy group. Illustrative examples of suitable aromatic hydroxy compounds include, but are not limited to, phenol, alkylphenols, alkoxyphenols, bisphenols, biphenols, and salicylic acid derivates (e.g., methyl salicylate).

The carbonylation catalyst composition present in the reaction mixture typically comprises a first metal source selected from a Group 8, 9 or 10 metal source. Typical Group 8, 9 or 10 metal sources include ruthenium sources, rhodium sources, palladium sources, osmium sources, iridium sources, platinum sources, and mixtures thereof. In one embodiment, about 1 ppm to about 10000 ppm of a Group 8, 9, or 10 metal source is present in the catalyst composition. In another embodiment, about 1 ppm to about 1000 ppm of a the Group 8, 9, or 10 metal source is present in the catalyst composition. In yet another embodiment of the present invention, about 1 ppm to about 100 ppm of a Group 8, 9, or 10 metal source is present in the catalyst composition. A typical Group 8, 9, or 10 metal source is a palladium source, including palladium compounds. As used herein, with respect to metal sources in general, the term "compound" includes inorganic, coordination and organometallic complex compounds. The compounds are typically neutral, cationic, or anionic, depending on the charges carried by the central metal and the coordinated ligands. Other common names for these compounds include complex ions (if electrically charged), Werner complexes, and coordination complexes. The Group 8, 9, or 10 metal source is typically present in the reaction mixture in a homogeneous form that is substantially soluble in the reaction mixture, or alternatively in a heterogeneous form which is substantially insoluble in the reaction mixture, including metal sources supported on substrates and polymer bound metal sources. Examples of suitable palladium sources include, but are not limited to, palladium sponge, palladium black, palladium deposited on carbon, palladium deposited on alumina, palladium deposited on silica, palladium halides, palladium nitrates, palladium carboxylates, palladium acetates, palladium salts of β-diketones, palladium salts of β-ketoesters, and palladium compounds containing at least one of the following ligands: carbon monoxide, amine, nitrite, nitrile, isonitrile, phosphine, phosphite, phosphate, alkoxide, alkyl, aryl, silyl or olefin.

As used herein, the term "inorganic co-catalyst"(IOCC) includes any catalyst component that contains a metal element, which is present in the catalyst composition in addition to the first metal source. Typically, one or two IOCC's are present in the catalyst composition, and thus are present in the reaction mixture as a second metal source and a third metal source, respectively. Typical IOCC's include, but are not limited to, compounds selected from the group consisting of Group 4 metal sources, Group 7 metal sources, Group 8 metal sources, Group 9 metal sources, Group 11 metal sources, Group 12 metal sources, Group 14 metal sources, Group 15 metal sources, Lanthanide sources, and mixtures thereof. Examples of IOCC sources include, but are not limited to, titanium sources, manganese sources, iron sources, cobalt sources, copper sources, zinc sources, lead sources, bismuth sources, and cerium sources. Suitable forms of IOCC sources include, but are not limited to, elemental metals, metal oxides, and metal compounds in stable oxidation states. For example, in one embodiment a first IOCC is initially present in the carbonylation catalyst composition as lead (II) oxide. Other suitable lead sources include, but are not limited to, lead halide compounds (e.g., lead (II) bromide), lead alkoxy compounds (e.g., lead (II) methoxide), lead aryloxy compounds (e.g., lead (II) phenoxide), organometallic lead compounds having at least one lead-carbon bond, (e.g., alkyl lead compounds such as tetraethyllead (IV)), and lead compounds containing at least one of the following ligands: carbon monoxide, amine, nitrite, nitrile, isonitrile, cyanide, phosphine, phosphite, phosphate, alkoxide, alkyl, aryl, silyl or olefin. Mixtures of lead sources are also suitable. The IOCC compounds are typically neutral, cationic, or anionic, depending on the charges carried by the central atom and the coordinated ligands. The IOCC compounds are typically present in the reaction mixture in a homogeneous form that is substantially soluble in the reaction mixture, or alternatively in a heterogeneous form which is substantially insoluble in the reaction mixture, including metal sources supported on substrates and polymer bound metal sources. In one embodiment, about 1 equivalent to about 1000 equivalents of at least one IOCC source, versus the amount of a Group 8, 9, or I0 metal source, is present in the reaction mixture. In another embodiment, about 1 equivalent to about 500 equivalents of at least one IOCC source, versus the amount of a Group 8, 9, or 10 metal source, is present in the reaction mixture. In yet another embodiment of the present invention, about 1 equivalent to about 100 equivalents of at least one IOCC source, versus the amount of a Group 8, 9, or 10 metal source, is present in the reaction mixture. For example, in one embodiment, about 1500 parts per million (ppm) of lead (II) oxide, versus about 27 ppm of palladium 2,4-pentanedionate, are present in the carbonylation catalyst composition in the reaction mixture.

Typically, the carbonylation catalyst composition in the reaction mixture further comprises at least one salt source. Illustrative examples of salt sources present in the carbonylation catalyst composition include, but are not limited to, carboxylates, acetates, benzoates, nitrates, phosphates, phosphites, tetraarylborate, sulfates, alkylsulfonates, arylsulfonates, alkali halides, alkaline-earth halides, guanidinium halides, and onium halides (e.g., ammonium halides, phosphonium halides, and sulfonium halides). Typical onium cations contain organic residues, which include C1–C20 alkyl, C6–C10 aryl, or alkyl-aryl combinations thereof. In one embodiment, about 1 equivalent to about 100000 equivalents of a salt source, versus the amount of a Group 8, 9, or 10 metal source, is present in the reaction mixture. In another embodiment, about 1 equivalent to about 10000 equivalents of a salt source, versus the amount of a Group 8, 9, or 10 metal source, is present in the reaction mixture. In yet another embodiment of the present invention, about 1 equivalent to about 1000 equivalents of a salt source, versus the amount of a Group 8, 9, or 10 metal source, is present in the reaction mixture. For example, in one embodiment, about 17000 ppm of tetraethylammonium bromide (TEAB), versus about 27 ppm of palladium 2,4-pentanedionate, are present in the carbonylation catalyst composition in the reaction mixture.

In one embodiment, the catalyst composition further comprises at least one activating solvent. Typically, about 1% to about 60% by volume of activating solvent, based on the total volume of the reaction mixture, is used. In another embodiment of the present invention, about 1% to about 40% by volume of activating solvent, based on the total volume of the reaction mixture is used. In yet another embodiment of the present invention, about 1% to about 10% by volume of activating solvent based on the total volume of the reaction mixture is used. Suitable activating solvents include, but are not limited to, polyethers (e.g. compounds containing two or more C—O—C linkages), carboxylic acid amides, sulfones, and nitriles. Polyethers are typically aliphatic or mixed aliphatic-aromatic polyethers. Suitable aliphatic polyethers include, but are not limited to, diethylene glycol dialkyl ethers such as diethylene glycol dimethyl ether (hereinafter "diglyme"), triethylene glycol dialkyl ethers such as triethylene glycol dimethyl ether (hereinafter "triglyme"), tetraethylene glycol dialkyl ethers such as tetraethylene glycol dimethyl ether (hereinafter "tetraglyme"), polyethylene glycol dialkyl ethers such as polyethylene glycol dimethyl ether and crown ethers such as 12-crown-4 (1,4,7,10-tetraoxacyclododecane), 15-crown-5 (1,4,7,10,13-pentaoxacyclopentadecane) and 18-crown-6 (1,4,7,10,13,16-hexaoxacyclooctadecane). Illustrative examples of mixed aliphatic-aromatic polyethers include, but are not limited to, diethylene glycol diphenyl ether and benzo-18-crown-6. Mixtures of polyethers are also suitable. Another example of a suitable activating solvent is a carboxylic acid amide. Typically, fully substituted aliphatic, fully substituted aromatic, or fully substituted heterocyclic amides (containing no NH groups including the amide nitrogen) are used. Illustrative examples of carboxylic acid amides include, but are not limited to, dimethylformamide, dimethylacetamide, dimethylbenzamide and N-methylpyrrolidinone. A further example of a suitable activating solvent is a sulfone. Suitable types of sulfones for the present invention include, but are not limited to, aliphatic sulfones, aromatic sulfones, and heterocyclic sulfones. Illustrative examples of suitable sulfones include, but are not limited to, dimethyl sulfone, diethyl sulfone, diphenyl sulfone, and sulfolane (e.g., tetrahydrothiophene-1,1-dioxide). In yet another embodiment of the present invention, a suitable activating solvent is a nitrile solvent. Suitable nitrile solvents include, but are not limited to, C2–C8 aliphatic or C7–C10 aromatic mononitriles or dinitriles. Illustrative mononitriles include, but are not limited to, acetonitrile, propionitrile, and benzonitrile. Illustrative dinitriles include, but are not limited to, succinonitrile, adiponitrile, and benzodinitrile. For example, in one embodiment the catalyst composition comprises acetonitrile, which is present at about 33 volume % based on the total volume of the reaction mixture.

In one embodiment of the present invention, the carbonylation catalyst composition further comprises at least one base source. Suitable types of base sources include, but are not limited to, basic oxides, hydroxides, mono-alkoxides, poly-alkoxides, monocyclic aryloxides, polycyclic aryloxides, and tertiary amines. Illustrative examples of suitable base sources include, but are not limited to, sodium hydroxide, lithium hydroxide, potassium hydroxide, tetraalkylammonium hydroxides (e.g. tetramethylammonium hydroxide, tetraethylammonium hydroxide, methyltributylammonium hydroxide, and tetrabutylammonium hydroxide) sodium phenoxide, lithium phenoxide, potassium phenoxide, tetraalkylammonium phenoxides (e.g. tetramethylammonium phenoxide, tetraethylammonium phenoxide, methyltributylammonium phenoxide, and tetrabutylammonium phenoxide), and triethyl amine. In one embodiment, about 1 equivalent to about 10000 equivalents of a base source, versus the amount of a Group 8, 9, or 10 metal source, is present in the reaction mixture. In another embodiment, about 1 equivalent to about 1000 equivalents of a base source, versus the amount of a Group 8, 9, or 10 metal source, is present in the reaction mixture. In yet another embodiment of the present invention, about 1 equivalent to about 500 equivalents of a base source, versus the amount of a Group 8, 9, or 10 metal source, is present in the reaction mixture.

An element in the present invention is the order in which changes to the reactions conditions are carried out. For example, in a typical oxidative carbonylation reaction where the reaction mixture has a temperature between about 80° C. and 120° C., and the reactor vessel is pressurized to between about 6 MPa and 9 MPa with carbon monoxide and oxygen, it is critical to the activity of the carbonylation catalyst composition that a decrease in the elevated reactor vessel pressure, especially if the decrease in pressure is to about atmospheric pressure, be preceded by a reduction in reaction mixture temperature to about 60° C. or lower. Failure to perform these changes in reaction conditions in this order, results in an irreversible reduction in activity of the catalyst composition, under the oxidative carbonylation conditions described above. Similarly, when re-establishing the original reaction conditions it is critical that the reactor vessel pressure be increased before the reaction mixture temperature is increased in order to retain a level of activity in the catalyst composition which is comparable to the level of activity which was present prior to any changes in reactor vessel pressure and reaction mixture temperature. In one embodiment, the final reactor vessel pressure and final reaction mixture temperature upon re-establishment of the carbonylation reaction, are about equivalent to the initial reactor vessel pressure and initial reaction mixture temperature.

The following examples are included to provide additional guidance to those skilled in the art in practicing the claimed invention. The examples provided are merely representative of the present invention. Accordingly, the following examples are not intended to limit the invention, as defined in the appended claims, in any manner. The examples listed in the following tables, show the usefulness of the present method in sustaining the catalytic activity of a catalyst composition comprising a palladium catalyst and various co-catalyst components, in the catalytic oxidative carbonylation of phenol to produce diphenyl carbonate (DPC). A metric used to illustrate usefulness of the present invention is the weight percent (wt %) of DPC produced during the course of the reaction. In the following examples, the reaction mixtures were periodically sampled, before and after changes to the reaction conditions, and the wt % DPC was measured by high performance liquid chromatography (HPLC) using an internal standard method. In comparative examples C1–C9, the reaction mixtures were exposed to the same changes in reaction conditions as the illustrative examples 1–3, but the changes were not necessarily performed in the same order as claimed in the present invention (e.g., the pressure in the reactor vessel was changed from P1 to P2 before reducing the temperature of the reaction mixture from T1 to T2, or alternatively without any reduction in the reaction mixture temperature T1). Comparative examples C1–C2 serve as control experiments, in which the reaction mixtures were treated under similar initial reaction conditions (e.g., T1 and P1) as the illustrative examples 1–3, and these conditions were maintained for the entire 2 hour reaction time with no changes to either the reactor vessel pressure or the reaction mixture temperature, and thus comparative examples C1–C2 demonstrate the level of catalytic activity which would typically be present in an uninterrupted oxidative carbonylation reaction. In addition to DPC, the reaction mixtures in the following examples comprise phenol, biphenols, bromophenols, polyhydroxyaromatic oligomers, other aromatic carbonates besides DPC, water, and the specific components of the carbonylation catalyst composition present in the various reaction mixtures as listed in Table 1. Tables 2 and 3, respectively summarize the changes in reaction conditions, and the wt % DPC present in each of the 30 minute time point samples for each of the following examples. For examples 1–3, a typical experimental procedure was as follows: a 450 mL Hastelloy-C autoclave, equipped with a stirrer, a condenser, gas inlet and exit ports capable of continuous gas feed at constant pressure, and optionally a perforated Teflon® basket mounted on the stir shaft above the level of the liquid which contained about 30 grams of 3 Å molecular sieves, was charged with about 60 grams of phenol, and the catalyst compositions described in Table 1. Palladium (Pd) was typically added as palladium (II) 2,4-pentanedionate, lead (Pb) was typically added as lead (II) oxide, titanium (T1) was typically added as titanyl (IV) oxide bis-2,4-pentanedionate, and the bromide source was typically added as either hexaethyl guanidinium bromide (HEGBr), tetraethyl ammonium bromide (TEAB), or sodium bromide (NaBr). In example 3, where acetonitrile (ACN) was used as an activating solvent, only about 40 grams of phenol was used with about 20 grams of acetonitrile. reactor was sealed and pressurized to between about 9 MPa and 11 MPa (e.g., P1) with 1150 standard litres per hour (SLPH) of carbon monoxide and 81 SLPH of oxygen.

The reaction temperature was elevated from room temperature to about 100° C. (e.g., T1) while stirring over about a 15 minute period. The reaction mixture was maintained under these initial conditions, P1 and T1, for about 30 minutes, and then the reaction mixture temperature was first reduced from T1 to T2, followed by a reduction in reactor vessel pressure from P1 to P2, the specific values of which are listed in Table 2. The reaction mixtures were maintained at P2 and T2 for about 5 minutes, and then the reactor vessel pressure was first raised from P2 to P3, followed by an increase in reaction mixture temperature from T2 to T3. The reaction mixtures were then maintained at the reaction conditions P3 and T3 under a continuous flow of 1150 SLPH of carbon monoxide and 81 SLPH of oxygen until the total reaction time reached about 2 hours. Samples of the reaction mixtures were taken periodically every 30 minutes.

Comparative examples C1–C2: the experimental procedure for the comparative control examples C1–C2 was similar to the procedure described above for examples 1–3, except that no changes in reaction conditions were performed throughout the entire 2 hour reaction time. The wt % DPC produce in these two control experiments was comparable to the wt % DPC produced in examples 1–3.

Comparative examples C3–C4: the experimental procedure for the comparative examples C3–C4, which are to be compared to examples 1–2, was similar to the procedure described above for examples 1–3, except that no change in reaction mixture temperature preceded either the decrease in reactor vessel pressure from P1 to P2 (e.g., T2=T1), or the re-establishment of the reactor vessel pressure from P2 to P3 (e.g., T3=T1), which resulted in a significant loss of catalytic activity. Example C4 is similar to C3, except that the reduction in reactor vessel pressure from P1 to P2 was carried out rapidly over a period of only 2 minutes, versus the 30 minutes taken in example C3.

Comparative example C5: the experimental procedure for the comparative example C5, which is to be compared to examples 1–2, was similar to the procedure described above for examples 1–3, except that the reduction in reactor vessel pressure from P1 to P2 preceded the reduction in reaction mixture temperature from T1 to T2, which resulted in a significant loss of catalytic activity.

Comparative example C6–C7: The experimental procedure for the comparative example C6–C7, which are to be compared to examples 1–2, was similar to the procedure described above for examples 1–3, except that value of T2 was not sufficiently low in order to maintain the activity of the catalyst composition. In the case of C7, the temperature of the reaction mixture was initially lowered to only 90° C. (e.g., T2) before the pressure of the reactor vessel was reduced to about 0.1 MPa, and in the case of example C8 the temperature of the reaction mixture was initially lowered to only 70° C. (e.g., T2) before the pressure of the reactor vessel was reduced to about 0.1 MPa. In both examples the activity of the catalyst composition was significantly reduced.

Comparative example C8: The experimental procedure for the comparative example C8, which is to be compared to example 3, was similar to the procedure described above for examples 1–3, except that the catalyst composition further comprised a activating solvent, and as in the case of examples C3–C4, no change in reaction mixture temperature preceded either the change in reactor vessel pressure from P1 to P2 (e.g., T2=T1), or the re-establishment of the reactor vessel pressure from P2 to P3 (e.g., T3=T1), which resulted in a significant loss of catalytic activity.

Comparative example C9: The experimental procedure for the comparative example C9, which is to be compared to example 3, was similar to the procedure described above for examples 1–3, except that the catalyst composition further comprised an activating solvent, and the temperature of the reaction mixture was initially lowered to only 70° C. (e.g., T2) before the pressure of the reactor vessel was reduced from P1 to P2, which was not sufficiently low to prevent significant loss of catalytic activity.

It is clear from example 1 –3 and comparative examples C1–C9 shown above, that the method of the present invention is effective at sustaining the catalytic activity of a catalyst composition during changes in reaction conditions in the catalytic production of aromatic carbonates.

TABLE 1

| | Catalyst Composition | | | | |
|---|---|---|---|---|---|
| Example | Pd (ppm) | 1st IOCC/eq. vs Pd | 2nd IOCC/ eq. vs Pd | Salt Source/ eq. vs Pd | Activating Solvent/ wt % |
| 1 | 29 | Pb/56 | — | HEGBr/630 | — |
| 2 | 25 | Pb/56 | — | TEAB/600 | — |
| 3 | 17 | Pb/57 | Ti/4 | NaBr/230 | ACN/33 |
| C1 | 25 | Pb/56 | — | TEAB/600 | — |
| C2 | 17 | Pb/56 | Ti/4 | NaBr/230 | ACN/33 |
| C3 | 27 | Pb/56 | — | TEAB/630 | — |
| C4 | 25 | Pb/56 | — | TEAB/600 | — |
| C5 | 25 | Pb/56 | — | TEAB/600 | — |
| C6 | 17 | Pb/93 | — | TEAB/833 | — |
| C7 | 16 | Pb/93 | — | TEAB/830 | — |
| C8 | 17 | Pb/57 | Ti/4 | NaBr/230 | ACN/33 |
| C9 | 17 | Pb/57 | Ti/4 | NaBr/230 | ACN/33 |

TABLE 2

| | | | | | | | Reaction mixture temperature during change from P1 to P2 (° C.) | time during change from P1 to P2 (hr) | Reaction mixture temperature during change from P2 to P3 (° C.) |
|---------|------------|-----------|------------|-----------|------------|-----------|---|---|---|
| Example | P1 (MPa) | T1 (° C.) | P2 (MPa) | T2 (° C.) | P3 (MPa) | T3 (° C.) | | | |
| 1  | 9  | 100 | 0.1 | 60  | 9  | 100 | 60  | 30 | 60  |
| 2  | 9  | 100 | 0.1 | 60  | 9  | 100 | 60  | 30 | 60  |
| 3  | 11 | 100 | 0.1 | 60  | 11 | 100 | 60  | 15 | 60  |
| C1 | 9  | 100 | —   | —   | —  | —   | —   | —  | —   |
| C2 | 11 | 100 | —   | —   | —  | —   | —   | —  | —   |
| C3 | 9  | 100 | 0.1 | 100 | 9  | 100 | 100 | 30 | 100 |
| C4 | 9  | 100 | 0.1 | 100 | 9  | 100 | 100 | 2  | 100 |
| C5 | 9  | 100 | 0.1 | 45  | 9  | 100 | 100 | 11 | 45  |
| C6 | 9  | 100 | 0.1 | 90  | 9  | 100 | 90  | 30 | 90  |
| C7 | 9  | 100 | 0.1 | 70  | 9  | 100 | 70  | 30 | 70  |
| C8 | 11 | 100 | 0.1 | 100 | 11 | 100 | 100 | 15 | 100 |
| C9 | 11 | 100 | 0.1 | 70  | 11 | 100 | 70  | 15 | 70  |

TABLE 3 wt % DPC as a function of reaction time

| Example | 0.5 hr | 1 hr | 1.5 hr | 2 hr |
|---------|--------|------|--------|------|
| 1  | 9.8 wt % | 13.4 | 19.6 | 23   |
| 2  | 6.8      | 11.3 | 18.3 | 23.7 |
| 3  | 3.8      | 5.4  | 14.7 | 18.0 |
| C1 | 7.3      | 18.7 | 21.9 | 22.3 |
| C2 | 6.5      | 13.1 | 15.3 | 16.1 |
| C3 | 5.3      | 6.2  | 7.5  | 8.8  |
| C4 | 4.2      | 5.2  | 7.7  | 9.7  |
| C5 | 3.3      | 6.2  | 6.6  | 7.1  |
| C6 | 4.9      | 5.3  | 6.2  | 7.0  |
| C7 | 3.6      | 4.6  | 5.6  | 6.0  |
| C8 | 5.2      | 6.0  | 8.3  | 9.1  |
| C9 | 3.6      | 4.2  | 8.8  | 12.8 |

What is claimed is:

1. A method for sustaining the catalytic activity of a carbonylation catalyst composition, after changes in reaction conditions, in a catalytic oxidative carbonylation reaction contained in a reactor vessel in which a reaction mixture comprising said carbonylation catalyst composition is disposed, said method comprising the following steps:

interrupting said carbonylation reaction with a first reaction condition changing step, which comprises first lowering the temperature of the reaction mixture from a first temperature T1, to a second temperature T2, followed by lowering the pressure in said reactor vessel from a first pressure P1, to a second pressure P2;

optionally, a resting step, which comprises maintaining said reaction mixture at said second temperature T2, and maintaining the pressure in said reactor vessel at said second pressure P2, for a predetermined amount of time; and re-establishing said carbonylation reaction with a second reaction condition changing step, which comprises first raising the pressure in said reactor vessel from said second pressure P2 to a third pressure P3, followed by raising the temperature of said reaction mixture from said second temperature T2 to a third temperature T3;

wherein the level of catalytic activity of said carbonylation catalyst composition under said third temperature T3, and said third pressure P3, is comparable to a level of catalytic activity which would be present in an equivalent catalytic oxidative carbonylation reaction in which the temperature and pressure were changed from said first temperature T1 and said first pressure P1 directly to said third temperature T3 and said third pressure P3, in the absence of said first reaction condition changing step, and said optional resting step.

2. The method of claim 1, wherein said carbonylation catalyst composition comprises a Group 8, 9, or 10 metal catalyst source.

3. The method of claim 2, wherein the Group 8, 9, or 10 metal catalyst source is a palladium source.

4. The method of claim 3, wherein said carbonylation catalyst composition further comprises at least one member selected from the group consisting of a first inorganic co-catalyst metal source, a second inorganic co-catalyst source, a salt source, an activating solvent, a base source, and any mixtures thereof.

5. The method of claim 4, wherein the first inorganic co-catalyst metal source is one member selected from the group consisting of a cobalt source, a manganese source, a copper source, and a lead source, wherein said first inorganic co-catalyst metal source is present in an amount between about 1 equivalent and about 1000 equivalents versus the amount of said Group 8, 9, or 10 metal catalyst source present.

6. The method of claim 5, wherein the second inorganic co-catalyst metal source is one member selected from the group consisting of a titanium source and a lead source, wherein said second inorganic co-catalyst metal source is present in an amount between about 1 equivalent and about 1000 equivalents versus the amount of said Group 8, 9, or 10 metal catalyst source present.

7. The method of claim 4, wherein the salt source is a halide source.

8. The method of claim 7, wherein the halide source is at least one member selected from the group consisting of a bromide source and a chloride source.

9. The method of claim 8, wherein the halide source is at least one member selected from the group consisting of an alkali metal bromide, an alkaline earth metal bromide, an alkylammonium bromide, a phosphonium bromide, a sulfonium bromide, a guanadinium bromide, an alkali metal chloride, an alkaline earth metal chloride, an alkylammonium chloride, a phosphonium chloride, a sulfonium chloride, a guanadinium chloride, and any mixtures thereof.

10. The method of claim 9, wherein the halide source is at least one member selected from the group consisting of sodium bromide, lithium bromide, potassium bromide, tetraethylammonium bromide, tetramethylammonium bromide, hexaethylguanidinium bromide, sodium chloride, lithium chloride, potassium chloride, tetraethylammonium chloride, tetramethylammonium chloride, hexaethylguanidinium chloride and any mixtures thereof, wherein said halide source is present in an amount between about 1 equivalent and about 100000 equivalents versus the amount of said Group 8, 9, or 10 metal catalyst source present.

11. The method of claim 4, wherein the activating solvent is at least one member selected from the group consisting of a polyether, a sulfone, a nitrile, a carboxylic acid amide, and any mixtures thereof.

12. The method of claim 11, wherein the polyether is at least one member selected from the group consisting of a diglyme, a triglyme, a tetraglyme, and any mixtures thereof, wherein said polyether is present in amount between about 1 volume % and about 60 volume % based on the total volume of the reaction mixture.

13. The method of claim 11, wherein the nitrile is acetonitrile, and is present in amount between about 1 volume % and about 60 volume % based on the total volume of the reaction mixture.

14. The method of claim 4, wherein the base source is at least one member selected from the group consisting of a basic oxide, a hydroxide, an aromatic monoalkoxide, an aromatic polyalkoxide, tertiary amines, and any mixtures thereof.

15. The method of claim 14, wherein the base source is at least one member selected from the group consisting of sodium hydroxide, lithium hydroxide, potassium hydroxide, tetramethylammonium hydroxide, tetraethylammonium hydroxide, methyltributylammonium hydroxide, tetrabutylammonium hydroxide,-sodium phenoxide, lithium phenoxide, potassium phenoxide, tetramethylammonium phenoxide, tetraethylammonium phenoxide, methyltributylammonium phenoxide, tetrabutylammonium phenoxide, triethyl amine, and any mixtures thereof, wherein said base source is present in an amount between about 1 equivalent and about 10000 equivalents versus the amount of Group 8, 9 or 10 metal catalyst source present.

16. The method of claim 1, wherein said reaction mixture further comprises at least one member selected from the group consisting of an aromatic hydroxy compound, an aromatic carbonate, water a polyaromatic oligomer, a halide source, a halogenated aromatic compound, and any mixtures thereof.

17. The method of claim 16 wherein the aromatic hydroxy compound is one member selected from the group consisting of phenol, bispheno-A, and methyl salicylate.

18. The method of claim 1, wherein said reactor vessel is a continuous stirred tank reactor.

19. The method of claim 1, wherein the first pressure P1 of said reactor vessel is between about 5 MPa and bout 15 MPa, and the first temperature T1 of said reaction mixture is between about, 50° C. and about 120° C.

20. The method of claim 19, wherein the second temperature T2 is between about 50% and about 75% of the first temperature T1, the second pressure P2 is between about 1% and about 25% of the first pressure P1, the third temperature T3 is between about 90% and about 110% of the first temperature T1, and the third pressure P3 is between about 90% and about 110% of the first pressure P1.

21. The method of claim 1, wherein the first temperature T1 is between about 90° C. and about 110° C., the first pressure P1 is between about 8 MPa and about 10 MPa, the second temperature T2 is between about 55° C. and about 60° C., the second pressure P2 is between about 0.1 MPa and about 1 MPa, the third temperature T3 is between 90° C. and about 110° C., and the third pressure P3 is between about 8 MPa and about 10 MPa.

22. The method of claim 1, wherein the reactor vessel is pressurized under a continuous-flow gas mixture comprising carbon monoxide and oxygen, or under a static gas mixture comprising carbon monoxide and oxygen.

23. The method of claim 22, wherein the percent oxygen in the continuous-flow gas mixtures is between about 0.1% to about 7%.

24. The method of claim 23, wherein the source of oxygen is air.

25. The method of claim 22, wherein the percent oxygen in the static gas mixtures is between about 0.1% to about 7%.

26. The method of claim 25, wherein the source of oxygen is air.

* * * * *